US012654261B2

(12) United States Patent　　(10) Patent No.:　US 12,654,261 B2

Chakraborty et al.　　(45) Date of Patent:　Jun. 16, 2026

(54) METHOD OF AND SYSTEM FOR MONITORING A QUALITY OF A WELD

(71) Applicant: GM GLOBAL TECHNOLOGY OPERATIONS LLC, Detroit, MI (US)

(72) Inventors: Debejyo Chakraborty, Novi, MI (US); Preston Hart, Detroit, MI (US); Mitchell Warchol, Columbus, MI (US); Spyros P. Mellas, Waterford, MI (US)

(73) Assignee: GM Global Technology Operations LLC, Detroit, MI (US)

( * ) Notice: Subject to any disclaimer, the term of this patent is extended or adjusted under 35 U.S.C. 154(b) by 0 days.

(21) Appl. No.: 18/975,140

(22) Filed: Dec. 10, 2024

(65) Prior Publication Data

US 2026/0158596 A1　　Jun. 11, 2026

(51) Int. Cl.
　*B23K 9/32*　　　(2006.01)
　*B23K 31/12*　　　(2006.01)
　*G01N 33/207*　　(2019.01)

(52) U.S. Cl.
　CPC ......... *B23K 31/125* (2013.01); *G01N 33/207* (2019.01)

(58) Field of Classification Search
　CPC .... B23K 9/095; B23K 20/123; B23K 31/125; G01N 33/207
　USPC ........................................................ 219/54
　See application file for complete search history.

(56) References Cited

U.S. PATENT DOCUMENTS 4,100,390　A　*　7/1978　Jackson ................. B23K 9/167
　　　　　　　　　　　　　　　　219/74

4,767,913　A　*　8/1988　Weber .................. B23K 37/006
　　　　　　　　　　　　　　　　219/136
4,877,940　A　*　10/1989　Bangs .................. B23Q 35/127
　　　　　　　　　　　　　　　　219/130.21
6,091,048　A　*　7/2000　Lanouette ................ B23K 9/32
　　　　　　　　　　　　　　　　219/130.21
6,583,386　B1　*　6/2003　Ivkovich .............. B23K 31/125
　　　　　　　　　　　　　　　　228/103
2005/0061778　A1*　3/2005　Arakawa ............ B23K 26/1436
　　　　　　　　　　　　　　　　219/121.6
2005/0173381　A1*　8/2005　Delzenne ............. B23K 10/006
　　　　　　　　　　　　　　　　219/121.41

(Continued)

FOREIGN PATENT DOCUMENTS

CN　　　　215880276　U　　　2/2022
EP　　　　4289546　A1　*　12/2023　............. B23K 31/02

(Continued)

*Primary Examiner* — Jimmy Chou
(74) *Attorney, Agent, or Firm* — Quinn IP Law

(57)　　　　ABSTRACT

A method of monitoring a quality of a weld includes collecting a first sample of a shielding gas flowing between a gas source and a welding device; analyzing the first sample to determine a shielding gas composition and thereby monitor a quality of the shielding gas; and forming the weld on a workpiece with the welding device to generate an evolution product of the weld. The method also includes, after collecting the first sample, collecting a second sample of the evolution product; and analyzing the second sample to determine an evolution product composition and thereby monitor the quality of the weld. A system includes the welding device; the gas source; an analyzer disposed between the welding device and the gas source; a first sampling device for collecting the first sample; and a second sampling device configured for collecting the second sample.

14 Claims, 2 Drawing Sheets

(56)     References Cited

U.S. PATENT DOCUMENTS

| | | | |
|---|---|---|---|
| 2009/0107960 A1* | 4/2009 | Hampton ............. | B23K 9/0956 |
| | | | 219/74 |
| 2009/0173726 A1* | 7/2009 | Davidson ............. | B23K 9/0953 |
| | | | 219/130.01 |
| 2011/0248000 A1* | 10/2011 | Barhorst ................ | B23K 9/164 |
| | | | 219/74 |
| 2013/0264317 A1* | 10/2013 | Hoffa ........................ | H05H 1/34 |
| | | | 219/121.53 |
| 2016/0001391 A1* | 1/2016 | Nacey .................. | B23K 31/125 |
| | | | 219/137 R |
| 2016/0101481 A1* | 4/2016 | Holverson .......... | B23K 9/0953 |
| | | | 219/121.72 |
| 2016/0136764 A1* | 5/2016 | Enyedy ................ | B23K 10/006 |
| | | | 219/74 |

FOREIGN PATENT DOCUMENTS

| | | |
|---|---|---|
| GB | 1512850 A | 6/1978 |
| JP | H1110335 A | 1/1999 |
| WO | 2023247065 A1 | 12/2023 |

* cited by examiner

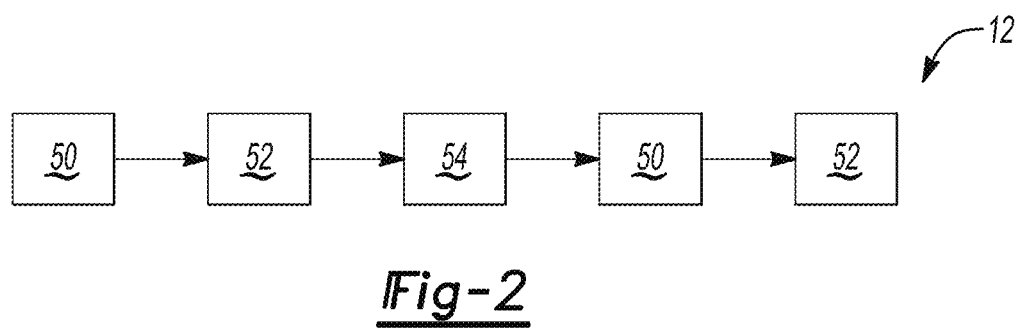
_Fig-2_
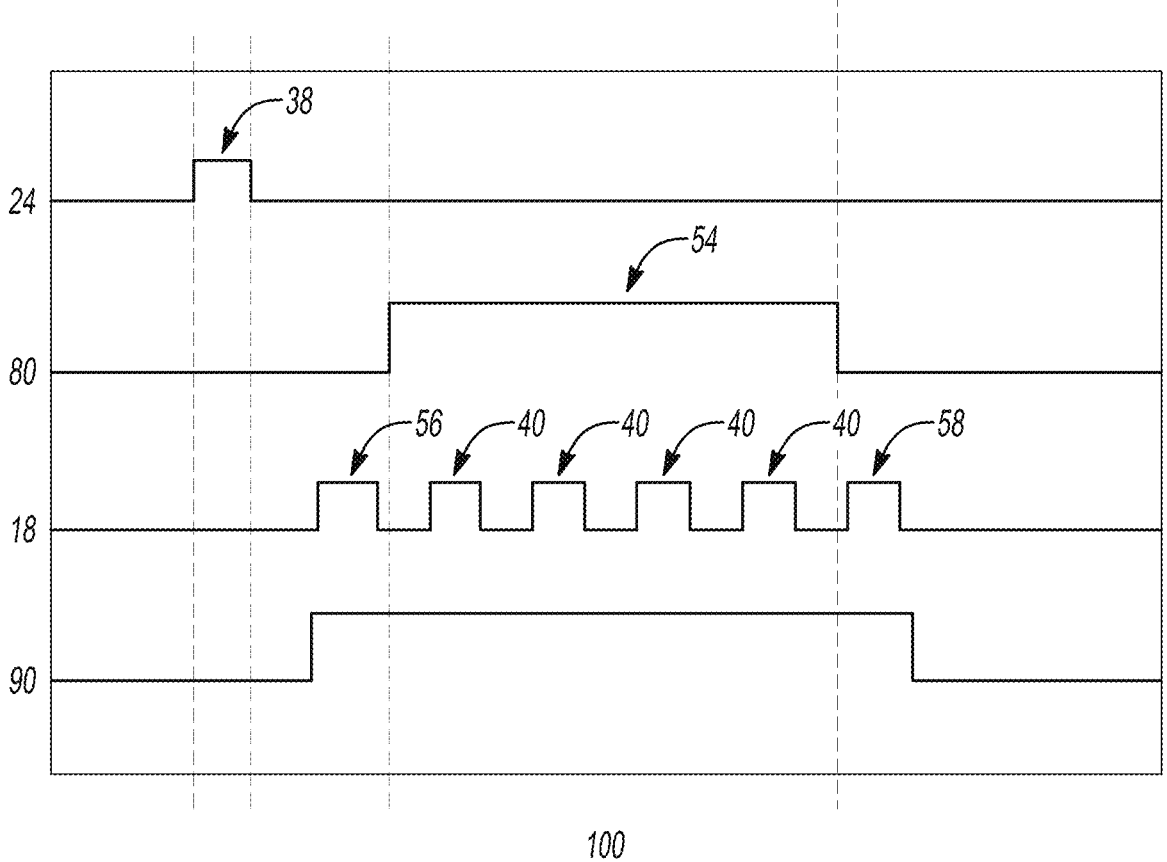
100
_Fig-3_
_Fig-4_

METHOD OF AND SYSTEM FOR MONITORING A QUALITY OF A WELD

INTRODUCTION

The disclosure relates to a method of and a system for monitoring a quality of a weld.

Welding processes, such as gas metal arc welding, metal inert gas welding, gas tungsten arc welding, brazing, laser welding, and soldering, are often useful for forming a weld with which to join metal or non-metal components together. For example, in some welding processes, a continuous, consumable solid wire electrode may be fed through a welding device, melt, form a weld pool, and solidify to thereby join the metal components together. A shielding gas may also be fed through the welding device to protect the weld pool from environmental contamination. In such operations, a quality of the formed weld may be determined by various process parameters.

SUMMARY

A method of monitoring a quality of a weld includes collecting a first sample of a shielding gas flowing between a gas source and a welding device; analyzing the first sample to determine a shielding gas composition and thereby monitor a quality of the shielding gas; and forming the weld on a workpiece with the welding device to generate an evolution product of the weld. After collecting the first sample, the method includes collecting a second sample of the evolution product; and analyzing the second sample to determine an evolution product composition and thereby monitor the quality of the weld.

In one aspect, the method may further include, before forming the weld, collecting a pre-weld sample of the evolution product.

In an additional aspect, the method may further include, after collecting the second sample, collecting a post-weld sample of the evolution product.

In a further aspect, analyzing the first sample may include comparing the shielding gas composition to a first standard.

In one aspect, analyzing the first sample may include identifying impurities present in the shielding gas.

In another aspect, analyzing the second sample may include comparing the evolution product composition to a second standard.

In an additional aspect, analyzing the second sample may include identifying impurities present in the evolution product.

In a further aspect, analyzing the second sample may include identifying an evolution rate of the evolution product.

In one aspect, forming the weld may include at least one of gas metal arc welding, gas tungsten arc welding, brazing, laser welding, soldering, and flux-cored arc welding the workpiece with the welding device.

In an additional aspect, analyzing the first sample may occur before the at least one of gas metal arc welding, gas tungsten arc welding, brazing, laser welding, soldering, and flux-cored arc welding the workpiece.

In one embodiment, a method of monitoring a quality of a weld includes collecting a first sample of a shielding gas flowing between a gas source and a welding device; analyzing the first sample to determine a shielding gas composition and thereby monitor a quality of the shielding gas; and measuring a flowrate of the shielding gas flowing between the gas source and the welding device. The method also includes forming the weld on a workpiece with the welding device to generate an evolution product of the weld. After collecting the first sample and concurrent to forming the weld, the method includes collecting a plurality of second samples of the evolution product. In addition, the method includes analyzing each of the plurality of second samples to determine an evolution product composition for each of the plurality of second samples and thereby monitor the quality of the weld.

In one aspect, the method may further include, before forming the weld, collecting a pre-weld sample of the evolution product.

In an additional aspect, measuring the flowrate may be concurrent to collecting the pre-weld sample and collecting the plurality of second samples.

In another aspect, the method may further include, after forming the weld, collecting a post-weld sample of the evolution product.

In a further aspect, measuring the flowrate may be concurrent to collecting the post-weld sample.

A system for monitoring a quality of a weld includes a welding device and a gas source configured for feeding a shielding gas to the welding device. The system also includes an analyzer disposed between the welding device and the gas source; a first sampling device disposed between the welding device and the gas source and configured for collecting and directing a first sample of the shielding gas to the analyzer; and a second sampling device disposed at the welding device and configured for collecting and directing a second sample of an evolution product generated by the welding device during formation of the weld to the analyzer.

In one aspect, the system may further include a flow sensor disposed between the analyzer and the welding device and configured for measuring a flowrate of the shielding gas.

In an additional aspect, the welding device may be configured for at least one of gas metal arc welding and gas tungsten arc welding a workpiece to form the weld.

In another aspect, the analyzer may be at least one of a universal gas analyzer, a vapor analyzer, and a particulate analyzer configured for determining a shielding gas composition of the shielding gas and an evolution product composition of the evolution product to identify impurities present in the shielding gas and the evolution product.

In a further aspect, a vehicle may include the weld formed by the system.

The above features and advantages, and other features and attendant advantages of this disclosure, will be readily apparent from the following detailed description of illustrative examples and modes for carrying out the present disclosure when taken in connection with the accompanying drawings and the appended claims. Moreover, this disclosure expressly includes combinations and sub-combinations of the elements and features presented above and below.

BRIEF DESCRIPTION OF THE DRAWINGS

FIG. 2 is a schematic illustration of a method of monitoring the quality of the weld formed by the system of FIG. 1.

FIG. 3 is a schematic illustration of a relationship between time, a sampling frequency, a gas flowrate, and a welding device power for the system of FIG. 1.

FIG. 4 is a schematic illustration of another embodiment of the method of FIG. 2.

DETAILED DESCRIPTION

Figure 1:
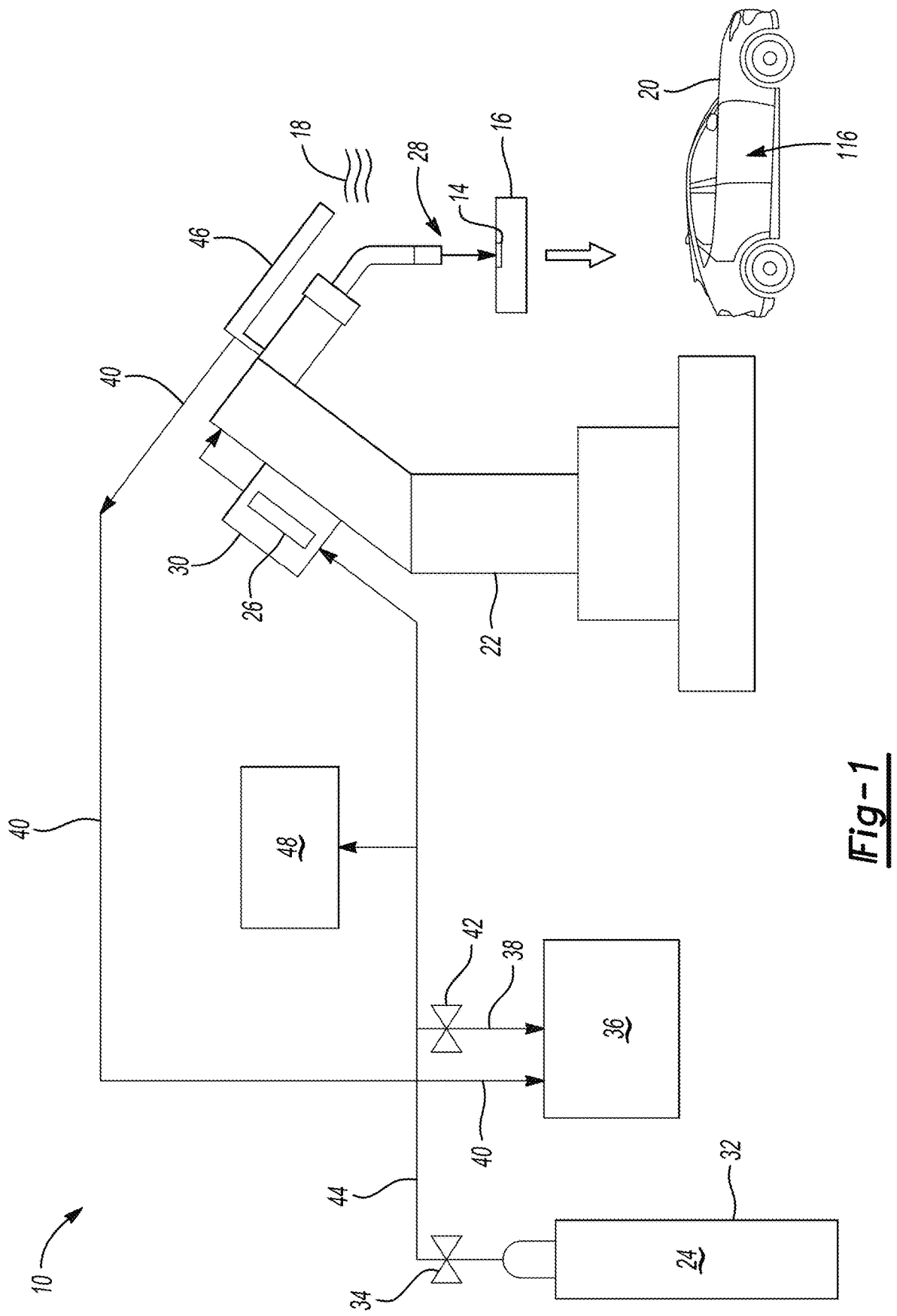
FIG. 1 is a schematic illustration of a side view of a system for monitoring a quality of a weld.

Referring to the Figures, wherein like reference numerals refer to like elements, a system 10 (FIG. 1) and a method 12, 112 (FIGS. 2 and 4) of monitoring a quality of a weld 14 (FIG. 1) are shown generally. The system 10 and method 12, 112 may be useful for applications requiring welds 14 having excellent quality to join together metal or non-metal components of a workpiece 16 (FIG. 1). In particular, the system 10 and method 12, 112 may be useful for monitoring and predicting the consistency, accuracy, and quality of a welding process and the resulting weld 14. More specifi- cally, and as set forth in more detail below, the method 12, 112 includes sampling and evaluating both a shielding gas composition and a composition of an evolution product 18 (FIG. 1), e.g., a gas and/or vapor, that evolves during formation of the weld 14 to thereby monitor the quality of the weld 14.

As such, the method 12, 112 and system 10 may be useful for welding processes for automotive applications such as, but not limited to, vehicles 20 (FIG. 1) including internal combustion engine vehicles, electric vehicles, hybrid vehicles, and the like. For example, the vehicle 20 may be a motor vehicle powered by a motive power source includ- ing at least one of an internal combustion engine, an electric motor, and an energy storage device. The vehicle 20 may include the weld 14 formed by the system 10 and method 12, 112 and may join together metal body components such as, but not limited to, door panels (shown generally at 116 in FIG. 1), trunk lids, body panels, body and chassis structures, structural elements, support components, and the like, or may join together metal components of electronics (not shown), such as, but not limited to, circuit boards, battery terminals, and electrodes. In other non-limiting examples, the vehicle 20 may include the weld 14 formed by the system 10 and method 12, 112 and may join together non-metal components such as trim, fascia, supports, panels, and the like.

Further, the vehicle 20 may be configured for autonomous or automated driving in which the vehicle 20 may be controlled or driven by technology including hardware and software, whether remote to the vehicle 20 or onboard the vehicle 20, that is capable of driving the vehicle 20 without active physical control by a human operator. For example, autonomous or automated driving tasks may include, but are not limited to, object and event detection, recognition, and classification; object and event response; maneuver plan- ning; steering, turning, lane-keeping, signaling, and lane changing; and acceleration and deceleration.

Alternatively, the method 12, 112, system 10, and vehicle 20 may be useful for welding processes for non-automotive applications such as, but not limited to, aerospace, aviation, marine, mass transportation, agricultural, industrial, and rail applications. For example, the vehicle 20 may be, but is not limited to, a commercial vehicle, industrial vehicle, passen- ger vehicle, automated guided vehicle (AGV), aircraft, watercraft, train, trolley, bus, or the like. It is also contem- plated that the vehicle 20 may be a mobile platform, such as an airplane, all-terrain vehicle (ATV), boat, personal move- ment apparatus, robot, and the like to accomplish the pur- poses of this disclosure. Further, the method 12, 112 and system 10 may be useful for applications requiring joining non-vehicular components with the weld 14, such as, but not limited to, general weldments, consumer goods, medical devices, electronics, structural elements, architectural ele- ments, building components, furniture, metal fabrications, and the like.

Referring now to FIG. 1, the system 10 for monitoring the quality of the weld 14 includes a welding device 22, such as a welding robot, arm, or welding gun. That is, although shown as a welding robot in FIG. 1, the welding device 22 may alternatively be a hand-held welding gun or other device. In one non-limiting example, the welding device 22 may be configured for at least one of gas metal arc welding and gas tungsten arc welding the workpiece 16 to form the weld 14 and generate the evolution product 18. In other non-limiting examples, the welding device 22 may be con- figured for brazing, e.g., gas metal arc brazing, or metal inert gas welding or laser welding or soldering the workpiece 16 to form the weld 14 and generate the evolution product 18. In still other non-limiting examples, the welding device 22 may be configured for tungsten inert gas welding or flux- cored arc welding. That is, the welding device 22 may be configured for component or material joining process that forms the weld 14 in conjunction with a shielding gas 24 (FIG. 1). Further, in still other non-limiting examples, the welding device 22 may form the weld 14 between similar or dissimilar metals, or between non-metals.

For example, with continued reference to FIG. 1, the welding device 22 may be repositionable and configured for combining a shielding gas 24 and a continuously-fed, con- sumable solid wire electrode (denoted generally at 26) at a welding tip 28 to form a weld pool and the weld 14 on the workpiece 16. For example, the welding device 22 may further include an electrode feeder 30 configured for feeding the solid wire electrode 26 and the shielding gas 24 to the welding tip 28. In addition, the welding device 22 may include a power source that provides constant voltage and direct current to melt the solid wire electrode 26 in the presence of the shielding gas 24 at the welding tip 28 to thereby form the weld pool and solid weld 14. In particular, during operation of the welding device 22, an electric arc may form between the solid wire electrode 26 and the workpiece 16, and the solid wire electrode 26 may melt and transfer to the workpiece 16 to form the weld pool. The shielding gas 24 may protect the molten metal weld pool from atmospheric conditions, and the weld pool may solidify to form the weld 14.

Referring again to FIG. 1, the system 10 also includes a gas source 32 configured for feeding the shielding gas 24 to the welding device 22. For example, the gas source 32 may be a standalone gas cylinder or bottle as shown or may be a dedicated conduit (not shown) from a gas tank and config- ured for delivering the shielding gas 24 to the welding device 22. The system 10 may also include a gas regulator 34 or valve to control or interrupt flow of the shielding gas 24 to the welding device 22. The gas source 32 may contain or enclose the shielding gas 24 to protect the shielding gas 24 from environmental contamination.

By way of non-limiting examples, the shielding gas 24 may include argon, carbon dioxide, nitrogen, oxygen, helium, hydrogen, and combinations thereof. For example, for welding aluminum and non-ferrous metal components of the workpiece 16, the shielding gas 24 may include argon. For welding steel metal components of the workpiece 16, the shielding gas 24 may include carbon dioxide. Other shield- ing gas 24 examples may include a combination or blend of argon and carbon dioxide; argon, carbon dioxide, and oxy- gen; argon and oxygen; and argon and helium. Nitrogen may be included as a component of the shielding gas 24 to minimize oxidation during welding, and helium may be included as a component of the shielding gas 24 for high-heat applications or to ensure excellent penetration of the weld 14.

As described with continued reference to FIG. 1, the system 10 also includes an analyzer 36 disposed between the welding device 22 and the gas source 32. The analyzer 36 may be configured for determining compositional amounts of components of one or more samples 38, 40 collected during the welding process or method 12, 112. In one example, the analyzer 36 may be at least one of a universal gas analyzer, a vapor analyzer, and a particulate analyzer configured for determining the shielding gas composition and an evolution product composition of the evolution product 18 to identify impurities present in the shielding gas 24 and the evolution product 18. In other non-limiting examples, the gas analyzer 36 may be a residual gas analyzer, a gas chromatography device, a custom gas analyzer, a metal oxide sensor, or another sensor configured for determining a molecular variety of the shielding gas composition and evolution product composition.

Referring again to FIG. 1, the system 10 also includes a first sampling device 42 disposed between the welding device 22 and the gas source 32. The first sampling device 42 is configured for collecting and directing a first sample 38 of the shielding gas 24 to the analyzer 36. For example, the first sample 38 may be collected from a feed line 44 that connects the gas source 32 and the electrode feeder 30 of the welding device 22 so that the shielding gas 24 may undergo a compositional analysis. By way of non-limiting examples, the first sampling device 42 may therefore be a valve or other diverter arranged to collect and direct the first sample 38 of the shielding gas 24 to the analyzer 36.

Similarly, as also shown in FIG. 1, the system 10 further includes a second sampling device 46 disposed at the welding device 22 and configured for collecting and directing a second sample 40 of the evolution product 18 generated by the welding device 22 during formation of the weld 14 to the analyzer 36. That is, as the weld 14 forms, the evolution product 18 or byproduct may be produced and may include at least one of an off-gas, vapor, and plasma generated during weld formation. For example, depending on the composition of the shielding gas 24, solid wire electrode, metal components of the workpiece 16, and coatings present on the metal components of the metal workpiece 16, the evolution product 18 may include at least one of metal oxides, such as, but not limited to, iron oxides, zinc oxides, manganese oxides, chromium oxides, nickel oxides, and aluminum oxides; gases, such as carbon monoxide, carbon dioxide, nitrogen oxides, and ozone; and decomposition products from coatings or oil residues, such as hydrocarbons, aldehydes, organic acids, isocyanates, and phosgene. The evolution product 18 may be gaseous, but may also include a plasma.

The second sampling device 46 is configured for collecting and directing the second sample 40 to the analyzer 36 and may therefore be disposed downstream of the electrode feeder 30, i.e., before the welding tip 28 of the welding device 22. For example, the second sample 40 may be collected from the second sampling device 46 or port disposed near the welding tip 28 of the welding device 22 to capture a portion of the evolution product 18 so that the evolution product 18 may undergo a compositional analysis. By way of non-limiting examples, the second sampling device 46 may therefore be an off-gas sampling device or valve or other diverter arranged to collect and direct the second sample 40 of the evolution product 18 to the analyzer 36. In another non-limiting example, the second sampling device 46 may be disposed in an air handling device such as a heating, ventilation, and air-conditioning device or other exhaust or air-exchange system.

As described with continued reference to FIG. 1, the system 10 may also include a flow sensor 48 disposed between the analyzer 36 and the welding device 22 and configured for measuring 60 a flowrate 90 (FIG. 3) of the shielding gas 24. For example, the flow sensor 48 may be disposed downstream of the analyzer 36 and upstream of the electrode feeder 30 on the feed line 44 that supplies the shielding gas 24 to the welding device 22. In another non-limiting example, the flow sensor 48 may be disposed in an air handling device such as a heating, ventilation, and air-conditioning device or other exhaust or air-exchange system. The flow sensor 48 may provide data regarding a velocity of the flow of the shielding gas 24 to the welding device 22.

Referring now to FIG. 2, the method 12 of monitoring the quality of the weld 14 includes collecting 50 the first sample 38 of the shielding gas 24 flowing between the gas source 32 and the welding device 22. That is, collecting 50 may include directing or diverting the shielding gas 24 toward the analyzer 36 by way of, for example, the first sampling device 42 before the shielding gas 24 reaches the welding device 22. In other words, the method 12 may include sampling the shielding gas 24 at a first point in the system 10 before the shielding gas 24 reaches the welding device 22 and is used to protect the weld pool from atmospheric conditions.

With continued reference to FIG. 2, the method 12 also includes analyzing 52 the first sample 38 to determine the shielding gas composition and thereby monitor the quality of the shielding gas 24. For example, analyzing 52 the first sample 38 may include comparing the shielding gas composition to a first standard. As such, analyzing 52 the first sample 38 may also include identifying impurities present in the shielding gas 24 and thereby monitoring the method 12 or welding process to ensure process accuracy and stability.

For example, if the shielding gas 24 is expected to include argon in a specified compositional percentage as set forth in the first standard, analyzing 52 may including comparing the first sample 38 to the first standard to determine whether the shielding gas composition matches the specified compositional percentage for argon. If, for example, the shielding gas composition includes argon at a lower compositional percentage than expected, the method 12 may include diagnosing or determining a source of the errant impurity. For example, if a regulator valve 34 on the gas source 32 is malfunctioning or if an incorrect shielding gas 24 is attached to the feed line 44 at the gas source 32, the method 12 may include diagnosing a reason for the compositional percentage disparity.

That is, the method 12 may include collecting 50 the first sample 38 to identify and confirm the shielding gas composition, identify the flowrate 90 (FIG. 3) of the shielding gas 24, identify impurities present in the shielding gas 24, and thereby predict the quality of the weld 14. For example, if the first sample 38 contains one or more impurities, the quality of the weld 14 may be negatively impacted. For such instances, the shielding gas 24 may be exchanged or replaced before forming 54 (FIG. 2) the weld 14 to minimize such quality impacts. As such, the method 12 may include correlating an incoming shielding gas 24 with the quality of the weld 14. Analyzing 52 the first sample 38 may also allow an operator to adjust or adapt one or more process parameters for forming 54 the weld 14 based on the shielding gas composition and the quality of the shielding gas 24. That is, the operator may change a weld schedule or parameters of the weld 14, e.g., time 100 (FIG. 3) or power settings of the welding device 22, to ensure that under the specific shielding gas conditions, the quality of the weld 14 is within tolerance.

Referring again to FIG. 2, the method 12 also includes forming 54 the weld 14 on the workpiece 16 with the welding device 22 to generate the evolution product 18 of the weld 14. That is, as described more specifically with reference to FIG. 3, forming 54 the weld 14 may include providing electrical power 80 (FIG. 3) to the welding device 22 for a specified time 100 (FIG. 3) to melt the solid wire electrode 26 in the presence of the shielding gas 24. Forming 54 the weld 14 may include at least one of gas metal arc welding, gas tungsten arc welding, brazing, laser welding, soldering, and flux-cored arc welding the workpiece 16 with the welding device 22. In one non-limiting example, forming 54 may include gas metal arc welding the workpiece 16 with the welding device 22. That is, forming 54 the weld 14 may include melting the solid wire electrode in the presence of the shielding gas 24 to form the weld pool and the evolution product 18, and solidifying the weld pool to form the weld 14 as set forth above.

Referring again to FIG. 2, analyzing 52 the first sample 38 may occur before the at least one of gas metal arc welding, gas tungsten arc welding, brazing, laser welding, soldering, and flux-cored arc welding the workpiece 16. That is, the method 12 may include first collecting 50 and analyzing 52 the first sample 38 before forming 54 the weld 14, which allows for ensuring a quality and consistency of the shielding gas 24 prior to welding.

More specifically, as best shown in FIG. 3, which illustrates a relationship between time 100 and several process parameters of the method 12, 112, the method 12 may further include, before forming 54 the weld 14, collecting 50 a pre-weld sample 56 of the evolution product 18 with the second sampling device 46. Since no weld formation is taking place when the pre-weld sample 56 is collected, collecting 50 the pre-weld sample 56 may ensure that the evolution product 18 at the welding tip 28 includes merely a combination of relatively pure shielding gas 24 and ambient environmental gases. That is, the method 12 may include collecting 50 the pre-weld sample 56 to also identify and confirm the shielding gas composition, for example by comparing the pre-weld sample 56 to the first sample 38 of shielding gas 24; identify the flowrate 90 (FIG. 3) of the shielding gas 24; identify impurities present in the shielding gas 24; and thereby predict the quality of the weld 14.

For example, if the pre-weld sample 56 contains one or more unexpected impurities or components other than the shielding gas 24 and ambient environmental gases, the quality of the weld 14 may be negatively impacted. For such instances, the shielding gas 24 may be exchanged or replaced before forming 54 the weld 14 to minimize such quality impacts. As such, the method 12 may include correlating an incoming shielding gas 24 with the quality of the weld 14. Analyzing 52 the pre-weld sample 56 may also allow an operator to adjust or adapt one or more process parameters for forming 54 the weld 14 based on the evolution product composition and the quality of the shielding gas 24.

Referring again to FIG. 2, the method 12 also includes, after collecting 50 the first sample 38, collecting 50 a second sample 40 of the evolution product 18. That is, collecting 50 may include directing or diverting the second sample 40 toward the analyzer 36 by way of, for example, the second sampling device 46 or port, as the evolution product 18 is generated during formation of the weld 14. In other words, the method 12 may include sampling the evolution product 18 at a second point in the system 10 while forming 54 the weld 14.

With continued reference to FIG. 2, the method 12 also includes analyzing 52 the second sample 40 to determine the evolution product composition and thereby monitor the quality of the weld 14. For example, analyzing 52 the second sample 40 may include comparing the evolution product composition to a second standard. As such, analyzing 52 the second sample 40 may also include identifying impurities or unexpected components present in the evolution product 18 and thereby monitoring the method 12 or welding process to ensure process accuracy and stability.

For example, if the evolution product 18 includes an unexpected oxide in a compositional percentage that is larger than a compositional percentage as set forth in the second standard, analyzing 52 may including comparing the second sample 40 to the second standard to determine how much the evolution product composition deviates from the expected second standard. If, for example, the evolution product composition includes an oxide at a greater compositional percentage than expected, the method 12 may include diagnosing or determining a source of the errant impurity or component. For example, if the welding device 22 is malfunctioning or if an incorrect shielding gas 24 is attached to the feed line 44 at the gas source 32 or if the electrode feeder 30 is incorrectly dispensing the solid electrode wire 26, the method 12 may include diagnosing a reason for the compositional percentage disparity.

Referring again to FIG. 2, analyzing 52 the second sample 40 may also include identifying an evolution rate of the evolution product 18. That is, the second sample 40 may provide data as to how fast and how well formation of the weld 14 is progressing and may provide another tool for monitoring the quality of the weld 14. If, for example, the evolution product 18 evolves or dissipates too quickly or too slowly or includes unexpected components, the quality of the weld 14 may suffer. Additionally or alternatively, if the evolution rate of the components of the evolution product 18 suddenly changes during formation of the weld 14, the quality of the weld 14 may be impacted. As such, analyzing 52 the second sample 40 may assist in predicting the quality of the weld 14.

Alternatively or additionally, analyzing 52 the second sample 40 may assist in identifying components of the evolution product 18 to ensure that the weld 14 is formed on intended types of workpieces 16 with intended types of coatings. That is, analyzing 52 the second sample 40 with the analyzer 36 may identify anomalies in metal types, e.g., aluminum workpieces 16 versus steel workpieces 16, and metal coatings disposed on the workpiece 16. Therefore, the method 12 may include collecting 50 and analyzing 52 the second sample 40 to identify the components of the workpiece 16; identify the evolution product composition; identify the evolution rate of various components of the evolution product 18; identify an existence of metal vapors or plasma and impurities present in the evolution product 18; and thereby monitor and predict process stability and the quality of the weld 14.

Referring now to FIGS. 2 and 3, the method 12 may further include, after collecting 50 the second sample 40, collecting 50 a post-weld sample 58 (FIG. 3) of the evolution product 18. The post-weld sample 58 may ensure that formation of the weld 14 is complete. That is, the evolution product 18 generated during forming 54 of the weld 14 may diminish after the weld 14 is formed and may mix with comparatively greater concentrations of shielding gas 24 such that the post-weld sample 58 includes a different composition than the second sample 40. For example, the post-weld sample 58 may include remnants of the evolution product 18 leftover from forming the weld 14, the shielding gas 24, and ambient environmental gases. As such, the method 12 may include collecting 50 the post-weld sample 58 to identify the end of forming 54 the weld 14. In other words, the method 12, 112 may further include, after forming 54 the weld 14, collecting the post-weld sample 58 of the evolution product 18, which may be mixed with shielding gas 24 and ambient environment to signal that the weld 14 is completely formed.

Referring now to FIG. 4, in another embodiment, the method 112 of monitoring the quality of the weld 14 includes, as set forth above, collecting 50 the first sample 38 of the shielding gas 24 flowing between the gas source 32 and the welding device 22; analyzing 52 the first sample 38 to determine the shielding gas composition and thereby monitor the quality of the shielding gas 24; measuring 60 the flowrate 90 (FIG. 3) of the shielding gas 24 flowing between the gas source 32 and the welding device 22; and forming 54 the weld 14 on the workpiece 16 with the welding device 22 to generate the evolution product 18 of the weld 14.

However, for this embodiment, as described with continued reference to FIGS. 3 and 4, the method 112 also includes, after collecting 50 the first sample 38 and concurrent to forming 54 the weld 14, collecting 50 a plurality of second samples 40 of the evolution product 18. That is, the method 112 may include collecting 50 multiple second samples 40 over the course of forming 54 the weld 14 to monitor and track the progress of weld formation. For example, depending upon the time 100 (FIG. 3) required to completely form the weld 14, collecting 50 may include sampling and analyzing 52 four or more second samples 40 as weld formation progresses. Although shown as equal collection intervals over time 100 in FIG. 3, the method 112 may alternatively include collecting 50 the plurality of second samples 40 at random intervals while forming 54 the weld 14.

Further, the method 112 includes analyzing 52 each of the plurality of second samples 40 to determine the evolution product composition for each of the plurality of second samples 40 to thereby monitor the quality of the weld 14. Therefore, the method 12 may include monitoring each of the respective evolution product compositions to determine whether weld formation is progressing as desired and expected. For example, if one or more of the respective evolution product compositions of the plurality of second samples 40 deviates from the second standard or from others of the evolution product compositions, the method 112 may indicate that weld formation is less than optimal. Conversely, if each of the plurality of second samples 40 has a similar respective evolution product composition that is within tolerance limits, the method 112 may indicate that weld formation is proceeding as desired and expected.

Referring again to FIGS. 3 and 4, for this embodiment, measuring 60 the flowrate 90 (FIG. 3) of the shielding gas 24 may be concurrent to collecting 50 the pre-weld sample 56 and collecting 50 the plurality of second samples 40. Likewise, measuring 60 the flowrate 90 may be concurrent to collecting 50 the final or post-weld sample 58. That is, a combination of measuring 60 and monitoring the flowrate 90 of the shielding gas 24 while collecting 50 the pre-weld sample 56, the plurality of second samples 40, and the post-weld sample 58 may ensure consistency and accuracy of forming the weld 14 and enhance and predict the quality of the weld 14.

Therefore, in summary, the method 12, 112 and system 10 may monitor and track the quality of the weld 14 and predict welding process upsets or inconsistencies. That is, the method 12, 112 may be useful for sensing a composition and flowrate 90 of incoming shielding gas 24 to predict welding process stability and accuracy and quality of the weld 14. Similarly, the method 12, 112 may also be useful for sensing a composition of evolved gas and vapor, i.e., the evolution product 18, during formation of the weld 14 to predict a quality of the weld 14. Such prediction and monitoring of the quality of the weld 14 may allow for in-situ classification and repair of in-process or completed welds 14.

The described embodiments of the present disclosure are intended to serve as non-limiting examples, and other embodiments may take various and alternative forms. In addition, the appended drawings are not necessarily to scale, and may present a somewhat simplified representation of various features of the present disclosure, including, for example, specific dimensions, orientations, locations, and shapes. Details associated with such features will be determined in part by the intended application and use environment of the described embodiments.

For purposes of the present description, unless specifically disclaimed, use of the singular includes the plural and vice versa, the terms "and" and "or" shall be both conjunctive and disjunctive, and the words "including", "containing", "comprising", "having", and the like shall mean "including without limitation". Moreover, words of approximation such as "about", "substantially", "generally", "approximately", etc., may be used herein in the sense of "at, near, or nearly at", or "within 0-5% of", or "within acceptable manufacturing tolerances", or logical combinations thereof. As used herein, a component that is "configured to" perform a specified function is capable of performing the specified function without alteration, rather than merely having potential to perform the specified function after further modification. In other words, the described hardware, when expressly configured to perform the specified function, is specifically selected, created, implemented, utilized, programmed, and/or designed for the purpose of performing the specified function. In addition, the use of ordinals such as first, second and third does not necessarily imply a ranked sense of order, but rather may merely distinguish between multiple instances of an act or structure.

The detailed description and the drawings or figures are supportive and descriptive of the present teachings, but the scope of the present teachings is defined solely by the claims. While some of the best modes and other embodiments for carrying out the present teachings have been described in detail, various alternative designs and embodiments exist for practicing the present teachings defined in the appended claims. Moreover, this disclosure expressly includes combinations and sub-combinations of the elements and features presented above and below.

What is claimed is:

1. A method of monitoring a quality of a weld, the method comprising:
   collecting a first sample of a shielding gas flowing between a gas source and a welding device;
   analyzing the first sample to determine a shielding gas composition and thereby monitor a quality of the shielding gas;
   forming the weld on a workpiece with the welding device to generate an evolution product of the weld;
   after collecting the first sample, collecting a second sample of the evolution product; and analyzing the second sample to determine an evolution product composition and an evolution rate of the evolution product and thereby monitor the quality of the weld.

2. The method of claim 1, further including, before forming the weld, collecting a pre-weld sample of the evolution product.

3. The method of claim 1, further including, after collecting the second sample, collecting a post-weld sample of the evolution product.

4. The method of claim 1, wherein analyzing the first sample includes comparing the shielding gas composition to a first standard.

5. The method of claim 1, wherein analyzing the first sample includes identifying impurities present in the shielding gas.

6. The method of claim 1, wherein analyzing the second sample includes comparing the evolution product composition to a second standard.

7. The method of claim 1, wherein analyzing the second sample includes identifying impurities present in the evolution product.

8. The method of claim 1, wherein forming the weld includes at least one of gas metal arc welding, gas tungsten arc welding, brazing, laser welding, soldering, and flux-cored arc welding the workpiece with the welding device.

9. The method of claim 8, wherein analyzing the first sample occurs before the at least one of gas metal arc welding, gas tungsten arc welding, brazing, laser welding, soldering, and flux-cored arc welding the workpiece.

10. A method of monitoring a quality of a weld, the method comprising:

collecting a first sample of a shielding gas flowing between a gas source and a welding device;

analyzing the first sample to determine a shielding gas composition and thereby monitor a quality of the shielding gas;

measuring a flowrate of the shielding gas flowing between the gas source and the welding device;

forming the weld on a workpiece with the welding device to generate an evolution product of the weld;

after collecting the first sample and concurrent to forming the weld, collecting a plurality of second samples of the evolution product; and analyzing each of the plurality of second samples to determine an evolution product composition and an evolution rate of the evolution product for each of the plurality of second samples and thereby monitor the quality of the weld.

11. The method of claim 10, further including, before forming the weld, collecting a pre-weld sample of the evolution product.

12. The method of claim 11, wherein measuring the flowrate is concurrent to collecting the pre-weld sample and collecting the plurality of second samples.

13. The method of claim 10, further including, after forming the weld, collecting a post-weld sample of the evolution product.

14. The method of claim 13, wherein measuring the flowrate is concurrent to collecting the post-weld sample.

* * * * *